United States Patent
Diehl et al.

(10) Patent No.: US 6,367,309 B1
(45) Date of Patent: Apr. 9, 2002

(54) METHOD OF PRODUCING AN INSULATION LAYER, AND SENSOR

(75) Inventors: Lothar Diehl, Stuttgart; Karl-Hermann Friese, Leonberg, both of (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 09/441,974

(22) Filed: Nov. 17, 1999

(30) Foreign Application Priority Data

Nov. 20, 1998 (DE) ......................................... 198 53 601

(51) Int. Cl.$^7$ ...................... G01N 33/497; G01N 27/26; H05B 3/10; C04B 35/03
(52) U.S. Cl. ...................... 73/23.32; 219/548; 204/426; 501/127
(58) Field of Search .............................. 73/31.06, 23.31, 73/23.32; 204/426, 427, 428; 422/110; 501/127; 219/548, 543

(56) References Cited

U.S. PATENT DOCUMENTS

| | | | | |
|---|---|---|---|---|
| 3,687,634 A | * | 8/1972 | Bancroft | ..................... 422/110 |
| 3,732,056 A | * | 5/1973 | Eddy et al. | ................. 425/352 |
| 4,092,264 A | * | 5/1978 | Tsang et al. | ........... 252/188.28 |
| 4,305,803 A | * | 12/1981 | Beyer et al. | ................ 204/426 |
| 4,609,454 A | * | 9/1986 | Ziegler | ........................ 204/427 |
| 4,636,293 A | * | 1/1987 | Bayha et al. | ................ 204/428 |
| 5,030,602 A | * | 7/1991 | Frey et al. | .................... 501/127 |
| 5,389,218 A | * | 2/1995 | Bonne et al. | ................ 205/785 |
| 5,389,225 A | * | 2/1995 | Aagard et al. | .............. 204/426 |
| 5,447,618 A | * | 9/1995 | Sugiyama et al. | .......... 204/426 |
| 5,753,893 A | * | 5/1998 | Noda et al. | ................. 219/548 |
| 5,889,261 A | * | 3/1999 | Boardman | .................. 219/543 |
| 5,898,360 A | * | 4/1999 | Lim | ........................... 338/254 |

FOREIGN PATENT DOCUMENTS

GB 94/29220 * 12/1994 ............. C01F/7/16

* cited by examiner

*Primary Examiner*—Hezron Williams
*Assistant Examiner*—Jay L. Politzer
(74) *Attorney, Agent, or Firm*—Michael J. Striker

(57) ABSTRACT

An insulation layer of a heating device for a sensor for determination of oxygen concentration in gas mixtures, in particular exhaust gasses of an internal combustion engine, is produced by applying a silicate-free insulation base material consisting only of barium oxide and/or strontium oxide with aluminum oxide to coat the heating device (50) and then heating the heating device with the insulation base material applied to it to temperatures of about 1350° to 1600° C. to form the insulation layer (60) by sintering. The sensor includes a Nernst measuring cell provided with a first electrode (16) and a second electrode (18) arranged in a solid electrolyte (20). The insulation layer (60) is arranged between the solid electrolyte (20) and the heating device (50).

6 Claims, 1 Drawing Sheet

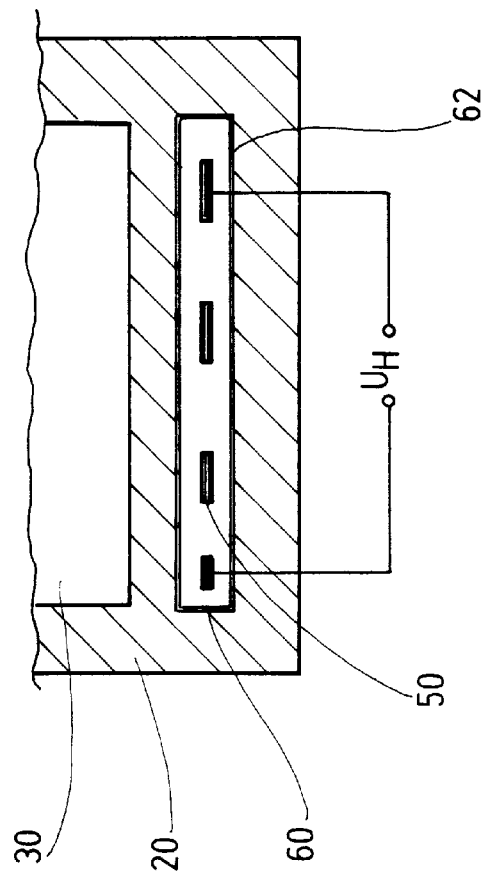
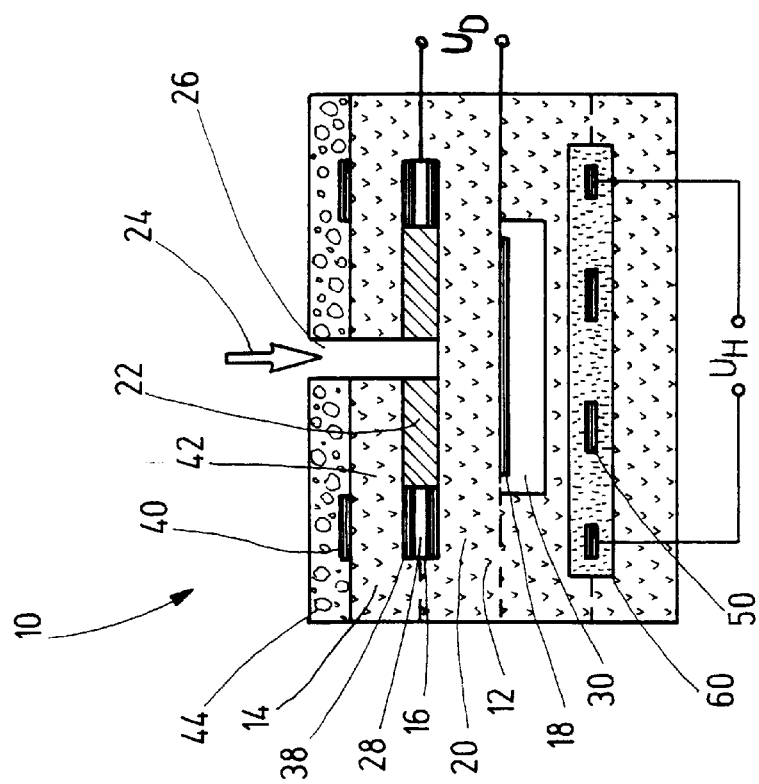

METHOD OF PRODUCING AN INSULATION LAYER, AND SENSOR

BACKGROUND OF THE INVENTION

The present invention relates to a method of producing an insulation layer, in particular for a heating device of a sensor, for determining an oxygen concentration in gas mixtures, in particular exhaust gasses of internal combustion engines. The present invention also relates to a sensor for determining an oxygen concentration in gas mixtures.

Sensors of the above-mentioned general type are known in the art. Such sensors serve for determination of the oxygen concentration in the exhaust gas of the internal combustion engine and adjustment of a fuel-air mixture for operating the internal combustion engine. The fuel-gas mixture can be provided in a so-called rich region. In other words, the fuel is in stochiometric excess, so that in the exhaust gas only a small quantity of oxygen with respect to other, partially non-burnt components is available. In the so-called poor region, in which the oxygen exceeds the air in the fuel-air mixture, an oxygen concentration in the exhaust gas is correspondingly high.

In order to determine the oxygen concentration in the exhaust gas, so-called lambda probes are known. In the poor region a lambda value is more than 1, while in the rich region it is less than 1, and in the stochiometric region a lambda value is equal to zero. A Nernst measuring cell of the sensor in a known manner produces a detection voltage, which is supplied to a switching device. The detection voltage depends on an oxygen concentration difference at an electrode exposed to the measuring gas and a reference electrode of the Nernst measuring cell exposed to a reference gas. The detection voltage increases or decreases with the oxygen concentration in the exhaust gas. A solid electrolyte body is arranged between the electrodes of the Nernst measuring cell and is conductive for the oxygen ions.

Such sensors must be heated in an active region of temperatures over approximately 300° C., for reaching the required ion conductivity of the solid electrolyte. The operational temperature is achieved by an additionally arranged heating device. The heating device has for example a meanderingly arranged heating conductor which is covered by an insulation layer from the solid electrolyte. The heated conductor is composed for example of a platinum conductor track.

The insulation layer is produced in known methods by addition of aluminum oxide and silicon dioxide-containing flux means, by sintering. The flux medium can be for example Celsian ($BaAl_2Si_2O_8$)-forming flux means initial material mixtures.

The insulation layer must satisfy the following requirements. On the one hand it must guarantee a sufficiently high mechanical stability to withstand loads occurring during the operation, on the other hand the insulation layer must be as homogenous as possible for minimizing locally occurring leakage current and suppressing damaging actions on the mechanic stability of the insulation layer and/or solid electrolyte. The known methods have the disadvantage in the homogenous structure of the insulation layer and a residual porosity which is technically difficult to reproduce.

Due to the required operational temperatures of 300° of the sensor, the electrical conductivity of the flux means-containing aluminum oxide increases, which forms the insulation layer. Partially, in hot condition a leakage current can occur, and the oxygen ions further flow into the solid electrolyte. With sufficiently open porosity of the insulation layer, air serves as the oxygen source. In the case that due to the reduced porosity the oxygen supply from the air is presented, the oxygen drains the solid electrolyte, or in other words the zirconium dioxide grate. The partial reduction of the solid electrolyte which can be visible as the occurring black coloring, provides for an electron conductivity which passes the sensor element as an avalanche. The partial reduction is accompanied by a phase conversion of the solid electrolyte. Because of the phase conversion from meta-stable tetragonal $ZrO_2$ grains into monokline $ZrO_2$ grains with greater volumes, released tension can lead to crack formation and thereby the heater can be mechanically damaged.

The porosity of the insulation layer in the known methods is significantly dependent from the dry grinding of the row mixture, from the distribution of the flux material barium and silicon, from the paste preparation and the screen printing conditions. The adjustment of the parameters is necessary and the reproducibility is limited, so that during the production an increased fraction is produced as a reject.

Furthermore, the occurrence of the above described leakage current leads to a shortened heater service life, and with the compact construction of the sensor can lead to a complete functional breakdown.

SUMMARY OF THE INVENTION

Accordingly, it is an object of the present invention to provide an insulation layer which avoids the disadvantages of the prior art.

It has been found that an insulation sheet can be produced with a homogenous porosity and in a reproducible way, when the production is performed with a mixture of only aluminum oxide, barium oxide and/or strontium oxide and/or during sintering by thermal disintegration of raw materials which form such oxides.

The additional barium oxide and/or strontium oxide can be provided in pure form or in the form of a compound. Preferably, the compound can be barium carbonate or strontium carbonate. The weight fraction of the barium or strontium carbonate during production of the insulation base material is between 3% and 20%. preferably of 9%. The other ingredient of the insulation base material is aluminum oxide, preferably γ-aluminum oxide.

The above-identified composition of the insulation base material does not contain silicon oxide, in contrast to the known methods. The fraction of barium oxide or strontium oxide-containing component is substantially increased. Thereby, on the one hand, the sintering temperature, which is required for the thermal production, is lowered below 1400° C., and, on the other hand, the formed insulation layer has a homogenous porosity. The utilization of glass-forming silicate flux material in the known methods led to an amorphous insulation layer. The glossy rigid phases close the pores of the heater insulation required for the oxygen supply and have increased ion conductivity (cation-conductivity).

The silicate-free insulation base material in accordance with the present invention makes it possible to avoid formation of amorphous structures during the thermal production. The addition of barium oxide and/or strontium oxide-containing compounds led in an unexpected manner to an especially sintered-active phase transition, which is caused by thermal decomposition with formation of special reactive oxides (Hedvall effect). In the same manner the phase transition of γ-aluminum oxide grains to alpha aluminum oxide grains increases the sinter activity of the insulation layer. The barium and/or strontium aluminate grains formed during sintering impart a high strength to the insulation layer. Furthermore, by addition of porogens, for example carbonates, the porosity of the insulation layer can be influenced in accordance with the desired objectives. Generally speaking, the use of the inventive insulation base material leads to a homogenous porosity of the insulation layer.

The preparation of the insulation base material is simplified when compared with the known methods, since the distribution of the porosity in the insulation layer substantially depends on the barium or strontium-containing components. The disadvantages which occur due to sinistrum-containing flux means as described herein above, could be avoided in the known methods only with consideration of numerous parameters, such as for example performing of dry milling or paste preparation.

Generally speaking, with the inventive method the service life of the sensor is substantially increased. The reduction of the disturbing leakage current with the resulting blackening of the solid electrolyte and crack formation in the insulation layer leads to a substantial reduction of rejects.

The novel features which are considered as characteristic for the present invention are set forth in particular in the appended claims. The invention itself, however, both as to its construction and its method of operation, together with additional objects and advantages thereof, will be best understood from the following description of specific embodiments when read in connection with the accompanying drawings.

BRIEF DESCRIPTION OF THE DRAWINGS

FIG. 1 is a view showing a section of a sensor in accordance with the present invention; and FIG. 2 is a view showing an enlarged portion of the inventive sensor.

DESCRIPTION OF PREFERRED EMBODIMENTS

FIG. 1 shows a sensor 10 in a cross-section with a measuring head. The sensor 10 is formed as a planar broad width sensor and has a plurality of individual superimposed layers, which can be structured for example by foil casting, punching, screen printing, laminating, cutting, sintering and the like. The production of the layer structure is not germane to the present invention and therefore it is not disclosed in detail, since it is well known.

The sensor 10 determines the oxygen concentration in exhaust gasses of an internal combustion engine, in order to produce a control signal for adjusting a fuel-oil mixture, with which the internal combustion engine operates. The sensor 10 has a Nernst measuring cell 12 and a pump measuring cell 14. The Nernst measuring cell 12 has a first electrode 16 and the second electrode 18, between which a solid electrolyte 20 is arranged. The electrode is is exposed to the exhaust gas 24 to be measured by diffusion through the diffusion barrier 22.

The sensor 10 has a measuring opening 26 which is loaded with the discharge gas 24. The diffusion barrier 22 extends at the base of the measuring opening 26. For forming a hollow chamber 28, it is arranged inside the electrode 16. The electrode 18 of the Nernst measuring cell 12 is associated with a reference air passage 30. A reference gas, for example air is available in the reference air passage. The solid electrolyte 20 is composed for example of yttrium oxide-stabilized zirconium oxide, while the electrodes 16 and 18 are composed for example of platinum and zirconium oxide.

The sensor 10 is connected with a not shown switching arrangement which serves for evaluation of signals of the sensor 10 and control of the sensor 10. The electrodes 16 and 18 are connected through suitable conductor tracks, which are subjected to a detection voltage UD of the Nernst measuring cell 12, connected with the switching arrangement.

The pump cell 14 is composed of a first electrode 38 as well as the second electrode 40 with a solid electrolyte 42 arranged between them. The solid electrolyte 42 is composed for example of an yttrium oxide-stabilized zirconium oxide, while the electrodes 38 and 40 are composed of platinum and zirconium oxide. The electrode 38 is also arranged in the hollow chamber 28 and thereby is exposed also to exhaust gas 24 through the diffusion barrier 22. The electrode 40 is covered with a protective layer 44. This protective layer is porous, so that the electrode 40 is directly exposed to the exhaust gas 24. The electrode 40 is connected with the switching arrangement, while the electrode 38 is connected with the electrode 16 and with it, is connected together to the switching device.

The sensor 10 further includes a heating device 50, which is formed by a so-called meandering heating conductor and is connected through suitable conductor tracks with the switching device. A heating voltage UH can be applied to the heating conductor by a regulating circuit, so that the heating device 50 is switchable on and off. The sensor 10 can be brought to an operational temperature over approximately 300° C. by the heating device 50. Due to the speed fluctuations of the exhaust gas 24 and/or temperature fluctuations of the exhaust gas 24, the sensor 10 is acted upon by the exhaust gas 24 with a predetermined fluctuating thermal energy.

Because of the heating of the sensor 10 with the exhaust gas 24, the heating device 50 must be switched on and off. In order to obtain the actual operational temperature of the sensor 10, the switching device has a not shown temperature measuring circuit. The measuring circuit produces a control signal for the heating device 50 according to the measured operational temperature.

An insulation layer 60 is located between the heating device 50 and the solid electrolyte 20. The insulation layer 60 is produced in the inventive method by sintering.

The conversion can be performed in the temperature region of 1350° C. to 1600° C., preferably 1400° C. The holding up time can fluctuate within broad limits. It can be advantageous to treat the insulation base material before the thermal treatment in dependence on the components to be used (for example dry milling or paste preparation). The execution can be performed under known screen printing conditions.

The composition of the insulation base material can be varied as follows. The weight fraction of the barium oxide and/or strontium oxide-containing components can be within the region between 3% and 20%, preferably 5–9%. The fraction of aluminum oxide can be for example correspondingly in the region between 80% and 97%, for example 91%. A source of barium oxide or strontium oxide are for example barium oxide and/or strontium oxide and/or compounds which form such oxide by thermal decomposition, for example carbonates.

The possibility of a technical execution of the method is illustrated in the following example of production of the insulation layer 60 with a barium carbonate fraction of 9 weight percent in the insulation base material.

It will be understood that each of the elements described above, or two or more together, may also find a useful application in other types of methods and constructions differing from the types described above.

While the invention has been illustrated and described as embodied in method of producing an insulation layer and sensor, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A sensor for measuring an oxygen concentration in a gas mixture, said sensor comprising sensor means for generating a detection voltage ($U_D$) depending on said oxygen concentration in said gas mixture;

a heating device (50) associated with said sensor means; and an insulation layer (60) in which said heating device is arranged, said insulation layer (60) being made by a method comprising the steps of:

a) providing an insulation base material consisting of a homogeneous mixture of aluminum oxide and at least one flux ingredient, wherein said at least one flux ingredient is selected from the group consisting of barium oxide, strontium oxide, compounds that generate barium oxide by thermal decomposition and compounds that generate strontium oxide by thermal decomposition, and wherein said insulation base material is silicate-free;

b) applying said insulation base material to said heating device (50) to coat the heating device (50); and c) heating said heating device (50) with said insulation base material applied thereto to a temperature of approximately 1350° to 1600° C. to sinter said insulation base material and thus form the insulation layer (60) on the heating device (50).

2. The sensor as defined in claim 1, wherein said insulation layer comprises from 3 to 20 percent by weight of said barium oxide or said strontium oxide.

3. The sensor as defined in claim 1, wherein said sensor means comprises a Nernst measuring cell provided with a first electrode (16) and a second electrode (18) arranged in a solid electrolyte (20) and said insulation layer is arranged between said solid electrolyte (20) and said heating device (50).

4. The sensor as defined in claim 1, wherein said heating is performed in an oxidizing atmosphere.

5. The sensor as defined in claim 1, wherein said sensor means comprises means for measuring said oxygen concentration in exhaust gases from an internal combustion engine.

6. The sensor as defined in claim 1, wherein said compounds that generate said barium oxide include barium carbonate and said compounds that generate said strontium oxide include strontium carbonate.

\* \* \* \* \*